(12) United States Patent
Hsu et al.

(10) Patent No.: US 7,913,556 B2
(45) Date of Patent: Mar. 29, 2011

(54) METHODS AND APPARATUS TO DETERMINE THE COMPRESSIBILITY OF A FLUID

(75) Inventors: Kai Hsu, Sugar Land, TX (US); Peter S. Hegeman, Stafford, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 469 days.

(21) Appl. No.: 12/137,058

(22) Filed: Jun. 11, 2008

(65) Prior Publication Data

US 2009/0308600 A1    Dec. 17, 2009

(51) Int. Cl.
*E21B 49/08* (2006.01)
*G01N 9/00* (2006.01)
*E21B 49/10* (2006.01)

(52) U.S. Cl. .................. 73/152.28; 73/32 A; 73/152.05; 73/152.16; 73/152.24; 73/152.27; 702/6

(58) Field of Classification Search .................. 73/32 A, 73/152.05, 152.16, 152.18, 152.23, 152.24, 73/152.27, 152.38, 152.51, 152.52; 702/6
See application file for complete search history.

(56) References Cited

U.S. PATENT DOCUMENTS

| | | | | |
|---|---|---|---|---|
| 3,252,131 | A * | 5/1966 | Vogel | 340/855.4 |
| 4,860,581 | A | 8/1989 | Zimmerman et al. | |
| 4,936,139 | A | 6/1990 | Zimmerman et al. | |
| 5,741,962 | A * | 4/1998 | Birchak et al. | 73/152.16 |
| 6,474,152 | B1 | 11/2002 | Mullins et al. | |
| 6,640,625 | B1 * | 11/2003 | Goodwin | 73/152.05 |
| 7,317,989 | B2 * | 1/2008 | DiFoggio et al. | 702/6 |
| 7,461,547 | B2 * | 12/2008 | Terabayashi et al. | 73/152.55 |
| 7,523,640 | B2 * | 4/2009 | DiFoggio et al. | 73/19.03 |
| 2003/0209066 | A1 * | 11/2003 | Goodwin | 73/152.05 |
| 2004/0045706 | A1 | 3/2004 | Pop et al. | |
| 2004/0123645 | A1 | 7/2004 | Storm, Jr. et al. | |
| 2009/0138216 | A1 * | 5/2009 | Africk | 702/54 |

FOREIGN PATENT DOCUMENTS

| | | | |
|---|---|---|---|
| EP | 2012117 A1 * | 1/2009 | |
| WO | 2006/039513 | 4/2006 | |
| WO | 2006/117604 | 11/2006 | |

OTHER PUBLICATIONS

Karstad, Eirik et al, Density Behavior of Drilling Fluids During High Pressure High Temperature Drilling Operations, SPE 47806, Jakarta, Indonesia, Sep. 7-9, 1998.
Dake, L.P., Fundamentals of Reservoir Engineering, Elsevier Scientific Publishing Company, 1978.
McCullagh, P. et al., Generalized Linear Model, 2nd Edition, Chapman and Hall, 1989.

* cited by examiner

*Primary Examiner* — John Fitzgerald
(74) *Attorney, Agent, or Firm* — Dave R. Hofman

(57) ABSTRACT

Example methods and apparatus to determine the compressibility of a fluid are disclosed. A disclosed example method includes capturing a fluid in a chamber, pressurizing the captured fluid to first and second pressures, measuring first and second values representative of first and second densities of the fluid while pressurized at respective ones of the first and second pressures, and computing a third value representative of a compressibility of the fluid using the first and second values.

20 Claims, 6 Drawing Sheets

METHODS AND APPARATUS TO DETERMINE THE COMPRESSIBILITY OF A FLUID

FIELD OF THE DISCLOSURE

This disclosure relates generally to fluid analysis and, more particularly, to methods and apparatus to determine the compressibility of a fluid.

BACKGROUND

Wellbores are drilled to, for example, locate and produce hydrocarbons. During a drilling operation, it may be desirable to perform evaluations of the formations penetrated by the wellbore. In some cases, a drilling tool is removed and a wireline tool deployed into the wellbore to test and/or sample the formation and/or fluids associated with the formation. In other cases, the drilling tool may be provided with devices to test and/or sample the surrounding formation and/or formation fluids without the need to remove the drilling tool from the wellbore. These samples or tests may be used, for example, to characterize hydrocarbons.

Formation evaluation often requires that fluid(s) from the formation be drawn into the downhole tool for testing, evaluation and/or sampling. Various devices, such as probes, are extended from the downhole tool to establish fluid communication with the formation surrounding the wellbore and to draw fluid(s) into the downhole tool. Fluid(s) passing through the downhole tool may be tested and/or analyzed to determine various downhole parameters and/or properties. Various properties of hydrocarbon reservoir fluids, such as viscosity, density and phase behavior of the fluid at reservoir conditions, may be used to evaluate potential reserves, determine flow in porous media and design completion, separation, treating, and metering systems, among others.

Additionally, samples of the fluid(s) may be collected in the downhole tool and retrieved at the surface. The downhole tool stores the formation fluid(s) in one or more sample chambers or bottles, and retrieves the bottles to the surface while, for example, keeping the formation fluid pressurized. These fluids may then be sent to an appropriate laboratory for further analysis, for example. Typical fluid analysis or characterization may include, for example, composition analysis, fluid properties and phase behavior. Additionally or alternatively, such analysis may be made at the wellsite using a transportable lab system.

SUMMARY

Example methods and apparatus to determine the compressibility of a fluid are disclosed. The example methods and apparatus disclosed herein to compute a fluid compressibility do not require the accurate measurement or control of the volume of a captured fluid that is being analyzed. As such, fluid compressibility may be determined using more easily constructed and/or less expensive fluid chambers because the finite compliance of the chamber(s) for different pressure regimes does not affect the accuracy of the determined fluid compressibilities. In examples described herein, the compressibility of a fluid as a function of pressure is determined using a plurality of fluid densities measured for respective ones of a plurality of pressures.

A disclosed example method includes capturing a fluid in a chamber, pressurizing the captured fluid to first and second pressures, measuring first and second values representative of first and second densities of the fluid while pressurized at respective ones of the first and second pressures, and computing a third value representative of a compressibility of the fluid using the first and second values.

A disclosed example fluid analysis apparatus includes a chamber, a pressure control unit to pressurize a fluid contained in the chamber at first and second pressures, a density sensor to measure first and second values representative of first and second densities of the fluid while pressurized at respective ones of the first and second pressures, and a compressibility module to compute a third value representative of a compressibility of the fluid based on the first and second values.

DETAILED DESCRIPTION

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness. Moreover, while certain preferred embodiments are disclosed herein, other embodiments may be utilized and structural changes may be made without departing from the scope of the invention.

Figure 1:
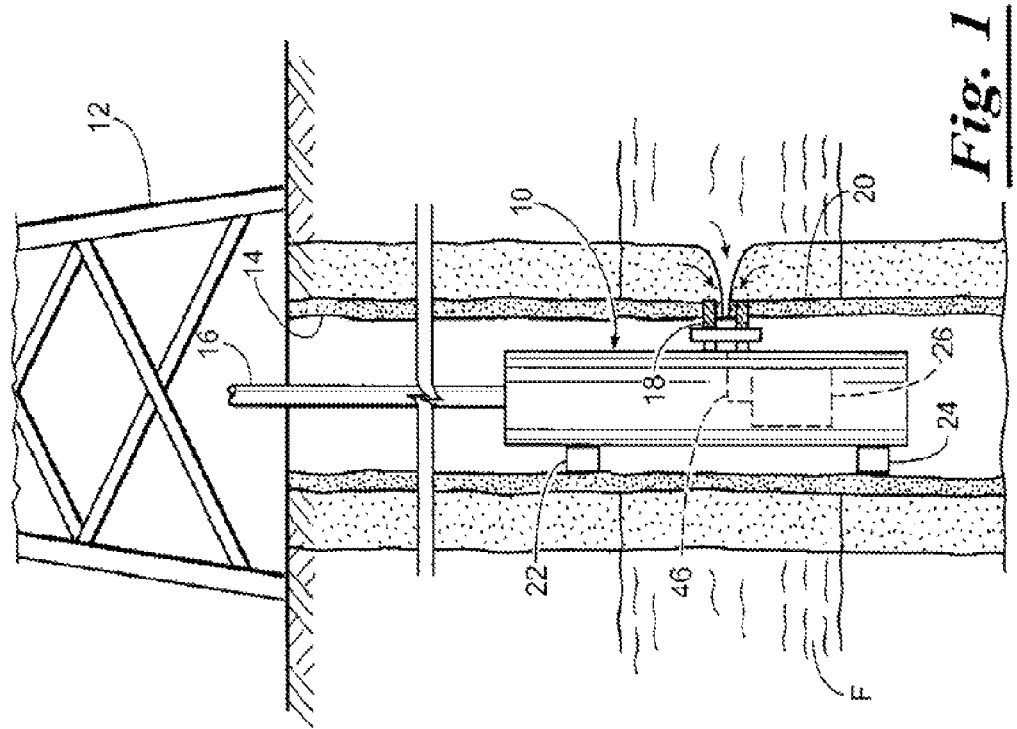
FIG. 1 is a schematic, partial cross-sectional view of a downhole wireline tool having an internal fluid analysis assembly with the wireline tool suspended from a rig.

FIG. 1 shows a schematic, partial cross-sectional view of an example downhole tool 10. The example downhole tool 10 of FIG. 1 is suspended from a rig 12 into a wellbore 14. The example downhole tool 10 can implement any type of downhole tool capable of performing formation evaluation, such as fluid analysis, fluid sampling, well logging, etc. The example downhole tool 10 of FIG. 1 is a wireline tool deployed from the rig 12 into the wellbore 14 via a wireline cable 16 and positioned adjacent to a formation F.

To seal the example downhole tool 10 of FIG. 1 to a wall 20 of the wellbore 14 (hereinafter referred to as a "wall 20" or "wellbore wall 20"), the example downhole tool 10 includes a probe 18. The example probe 18 of FIG. 1 forms a seal with the wall 20 and draws fluid(s) from the formation F into the downhole tool 10 as depicted by the arrows. Backup pistons 22 and 24 assist in pushing the example probe 18 of the downhole tool 10 against the wellbore wall 20.

To perform fluid analysis, the example downhole tool 10 of FIG. 1 includes a fluid analysis assembly 26 constructed in accordance with the present disclosure. The example fluid analysis assembly 26 of FIG. 1 performs formation evaluation and/or analysis of downhole fluids, such as the formation fluids extracted or drawn from the formation F. The example fluid analysis assembly 26 receives the formation fluid(s) from the probe 18 via an evaluation flowline 46. Example manners of implementing the example fluid analysis assembly 26 of FIG. 1 are described below in connection with FIGS. 3 and 4.

Figure 2:
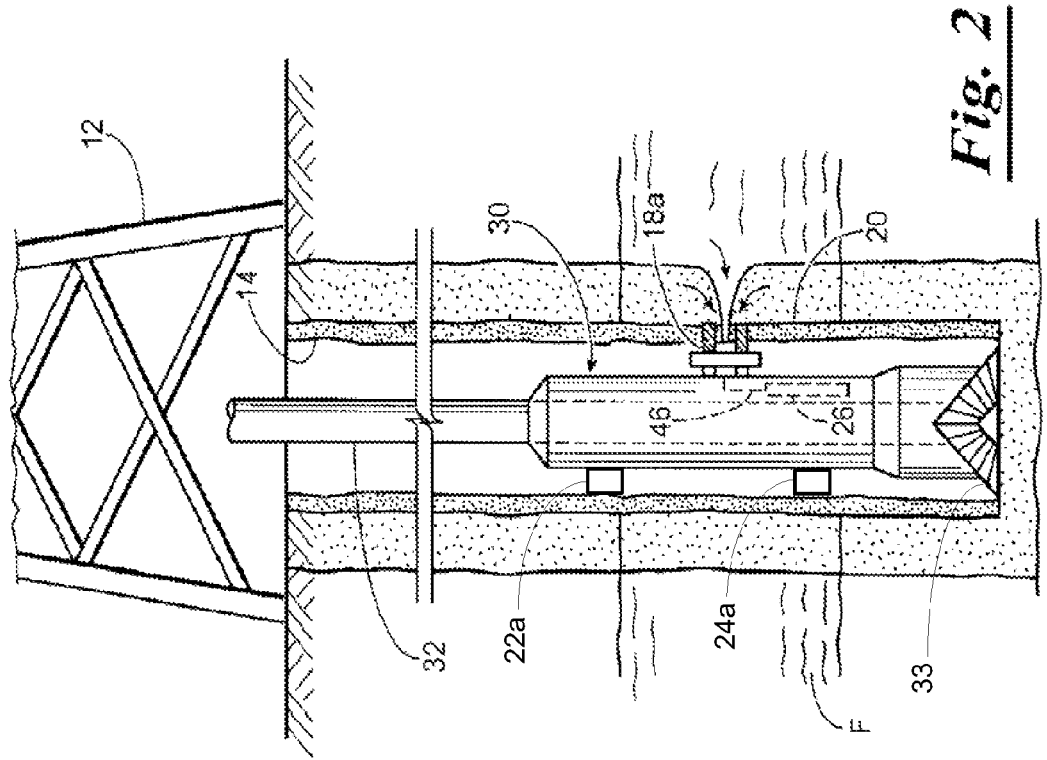
FIG. 2 is a schematic, partial cross-sectional view of a downhole drilling tool having an internal fluid analysis assembly with the downhole drilling tool suspended from a rig.

FIG. 2 shows a schematic, partial cross-sectional view of another example of a downhole tool 30. The example downhole tool 30 of FIG. 2 can be conveyed among one or more (or itself may be) of a measurement-while-drilling (MWD) tool, a logging-while-drilling (LWD) tool, or other downhole tool that are known to those skilled in the art. The example downhole tool 30 is attached to a drill string 32 and a drill bit 33 driven by the rig 12 to form the wellbore 14.

To seal the example downhole tool 30 of FIG. 2 to the wall 20 of the wellbore 14, the downhole tool 30 includes a probe 18a. The example probe 18a of FIG. 2 forms a seal with the wall 20 and draws fluid(s) from the formation F into the downhole tool 30 as depicted by the arrows. Backup pistons 22a and 24a assist in pushing the example probe 18a of the downhole tool 30 against the wellbore wall 20. Drilling is stopped before the probe 18a is brought in contact with the wall 20.

To analyze fluid(s), the example downhole tool 30 of FIG. 2 also includes a fluid analysis assembly 26. The example fluid analysis assembly 26 of FIG. 2 performs formation evaluation and/or analysis of downhole fluids, such as the formation fluids extracted or drawn from the formation F. The example fluid analysis assembly 26 receives the formation fluid(s) from the probe 18a via the evaluation flowline 46. Example manners of implementing the example fluid analysis assembly 26 of FIG. 2 are described below in connection with FIGS. 3 and 4.

While FIGS. 1 and 2 depict the fluid analysis assembly 26 in example downhole tools 10 and 30, a fluid analysis assembly 26 may be provided or implemented at the wellsite, or an offsite facility for performing fluid tests. By positioning the fluid analysis assembly 26 in a downhole tool 10, 30, real-time data may be collected concerning downhole fluids. However, it may also be desirable and/or necessary to test fluids at the surface and/or offsite locations. In such cases, the fluid analysis assembly 26 may be positioned in a housing transportable to a desired location. Alternatively, fluid samples may be taken to a surface or offsite location and tested in a fluid analysis assembly 26 at such a location. Data and test results from various locations may be analyzed and compared.

Figure 3:
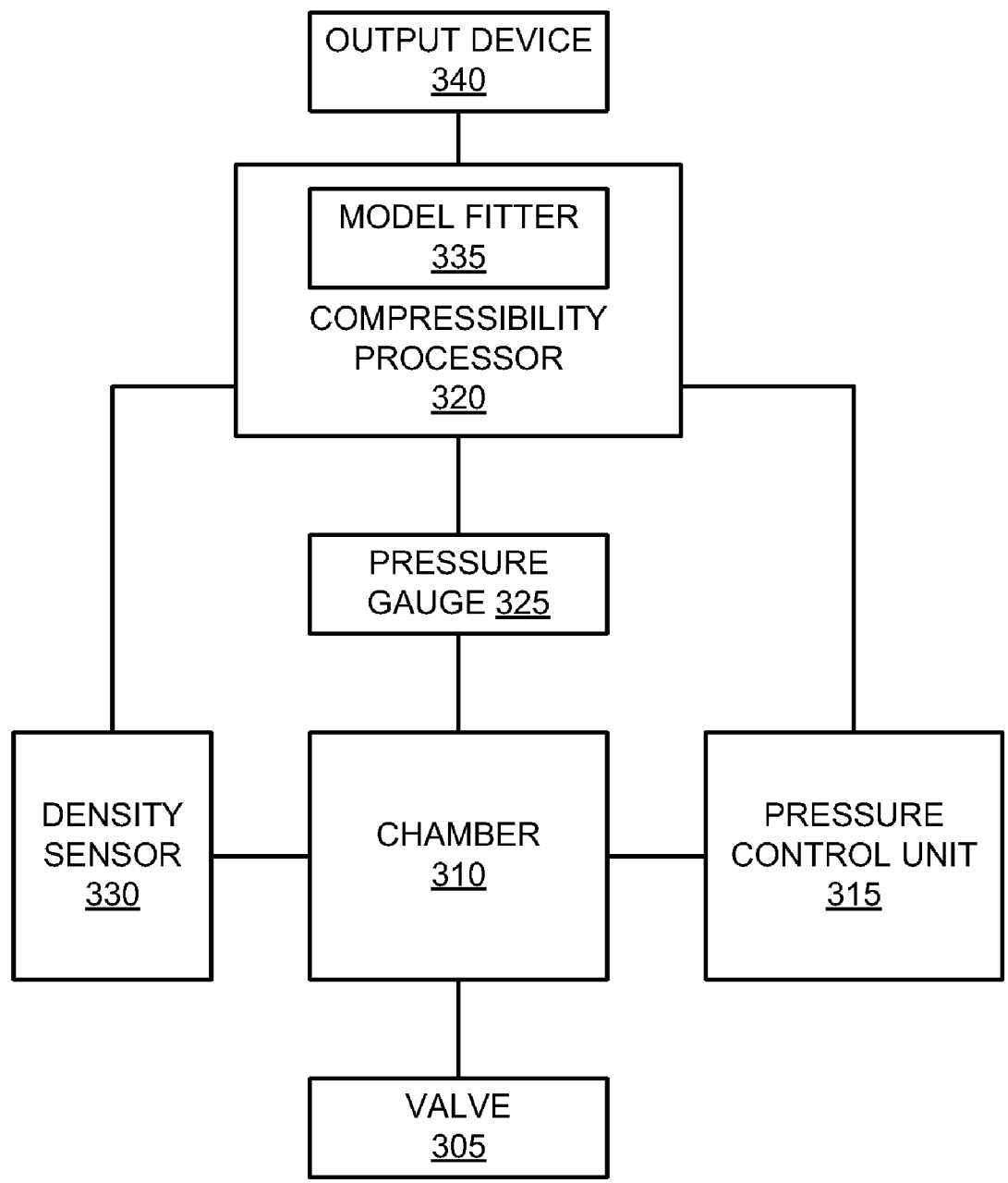
FIG. 3 is a schematic diagram of an example fluid analysis assembly.

FIG. 3 is a schematic diagram of an example fluid analysis assembly 300. The example fluid analysis assembly 300 of FIG. 3 may be used to implement either or both of the example fluid analysis assemblies 26 of FIGS. 1 and 2, and/or may be used to perform fluid analysis at the surface, at a wellsite, in a transportable lab, and/or in a fixed-location facility.

To capture a fluid, the example fluid analysis assembly 300 of FIG. 3 includes one or more valves (one of which is designated at reference numeral 305) and a chamber 310. The example chamber 310 of FIG. 3 is any type of chamber, vessel, container, bottle, cell and/or flowline suitable for holding, containing and/or otherwise retaining a pressurized fluid during analysis. The example valve 305 is any type of valve that is operable and/or controllable to allow fluid(s) to enter and/or exit the chamber 310. In some examples, one valve 305 is used to allow fluid(s) to enter the chamber 310, and another valve (not shown) is used to allow fluid(s) to exit the chamber 310.

To pressurize a fluid captured in the example chamber 310, the example fluid analysis assembly 300 of FIG. 3 includes any type of pressure control unit 315. Under the control of a compressibility processor 320, the example pressure control unit 315 of FIG. 3 is configurable and/or controllable to pressurize a fluid captured in the chamber 310 across a range of pressures. As used herein, the phrase "pressurize a fluid" is used to mean that the fluid is held and/or maintained at a specific pressure, and does not imply that the pressure of the fluid was increased to reach the pressure. The example pressure control unit 315 is any type of assembly or device capable of communicating with the chamber 310 and continuously changing (and/or step-wise changing) the pressure of a fluid within the chamber 310. An example manner of implementing the example pressure control unit 315 is described below in connection with FIG. 4. Another example pressure control unit 315 is a syringe pump that can compress or expand the volume, causing the pressure in the chamber 310 to increase or decrease, accordingly.

To measure a pressure of a fluid, the example fluid analysis assembly 300 of FIG. 3 includes any type of pressure gauge 325. The example pressure gauge 325 of FIG. 3 measures and/or senses the pressure of a fluid captured in the chamber 310. By monitoring an output of the pressure gauge 325 that represents the pressure of the fluid captured in the chamber 310 and controlling the pressure control unit 315, the compressibility processor 320 can control, direct and/or maintain the fluid captured in the chamber 310 at a desired pressure. An example pressure sensor 325 is a micro-sapphire sensor.

To measure a density of a fluid, the example fluid analysis assembly 300 of FIG. 3 includes any type of density sensor 330. The example density sensor 330 of FIG. 3 measures and/or senses the density of a fluid captured in the chamber 310. An example density sensor 330 comprises a vibrating rod, and electronics for actuation and detection. As is well known in the art, the resonance characteristic(s) of a vibrating rod oscillating in a fluid may used to determine, measure, compute and/or otherwise detect the density of the fluid in which the vibrating rod oscillates. An example density sensor 330 is described in European Patent No. EP 1804048 entitled "A density and viscosity sensor," which is hereby incorporated by reference in its entirety.

To determine fluid compressibility, the example fluid analysis assembly 300 of FIG. 3 includes the example compressibility processor 320. The example compressibility processor 320 of FIG. 3 controls the example pressure control unit 315 to pressurize a fluid captured in the chamber 310 at a set of pressures $p=\{p_1, \ldots, p_n\}$ and records corresponding fluid densities $\rho=\{\rho_1, \ldots \rho_n\}$ measured by the density sensor 330 for respective ones of the pressures p. The fluid may be pressurized at the pressures p is any order or sequence such as, for example, at a set of successively increasing or decreasing pressures. Collectively, the pressures p and the fluid densities ρ form a plurality of pressure-density data pairs. Such pressure-density data pairs may be plotted as shown in the example graph of FIG. 6.

Using two or more pressure-density data pairs, the example compressibility processor 320 computes a corresponding fluid compressibility. The compressibility c of a fluid can be expressed mathematically as:

$$c = -\frac{1}{v}\frac{\partial v}{\partial p}, \quad \text{EQN (1)}$$

where v is the volume of the chamber 310, and p is the pressure of the fluid contained in the chamber 310. In the examples described herein, the volume v also includes the volume(s) of a flowline used to establish fluid communication between the valve 305 and the chamber 310, a flowline used to establish fluid communication between the density sensor 330 and the chamber 310, a flowline used to establish fluid communication between the pressure gauge 325 and the chamber 310, and/or any portion of the fluid contained in a portion of the pressure control unit 315 (e.g., in a displacement chamber). As used herein, the phrase "fluid contained in the chamber 310" refers to collectively to all of these volumes.

The density $\rho$ of a fluid captured in the chamber 310 is defined as:

$$\rho = \frac{m}{v}, \quad \text{EQN (2)}$$

where m is the mass of the fluid contained in the chamber 310. In the examples described herein, the mass m also includes the mass of any fluid contained a flowline used to establish fluid communication between the valve 305 and the chamber 310, a flowline used to establish fluid communication between the density sensor 330 and the chamber 310, a flowline used to establish fluid communication between the pressure gauge 325 and the chamber 310, and/or any portion of the pressure control unit 315 (e.g., in a displacement chamber). If the example pressure control unit 315 also contains a portion of the fluid being analyzed (e.g., in a displacement chamber of the pressure control unit 315), then the mass m also includes the mass of the fluid that is contained in the pressure control unit 315. Because the example fluid analysis assembly 300 of FIG. 3 is a closed system (i.e., no fluid enters or leaves while the fluid is being analyzed), the mass m of the fluid remains constant. Using EQN (1) and EQN (2), the compressibility c of the fluid can be expressed as:

$$c = -\frac{1}{\rho}\frac{\partial \rho}{\partial p} = \frac{\partial}{\partial p}\ln\rho. \quad \text{EQN (3)}$$

For liquid or gaseous fluids, compressibility c is a function of pressure p because the density $\rho$ is a function of pressure p. Using two pressure-density data pairs $(p_r, \rho_r)$ and $(p_s, \rho_s)$, the compressibility c of a fluid can be computed using a discretized form for EQN (3), which may be expressed as:

$$c = \frac{\ln\rho_r - \ln\rho_s}{p_r - p_s}, \quad \text{EQN (4)}$$

where the computed compressibility c of the fluid is associated with the average of the pressures $p_r$ and $p_s$.

While the example mathematical expression of EQN (4) may be used to compute the compressibility c of a fluid, higher-order models may be used to improve the accuracy of computed compressibilities c, to reduce or eliminate the effects of noisy measurements, and/or to compute compressibility as a function of pressure. An example model comprises a second-order polynomial model, which may be expressed mathematically as:

$$\rho_{model}(p) = a_1 + a_2(p-p_0) + a_3(p-p_0)^2, p_0 - p_w/2 \leq p \leq p_0 + p_w/2 \quad \text{EQN (5)}$$

where $\rho(p)$ is fluid density for a particular pressure p and $p_0$ and $p_w$ corresponding to a center pressure and width of a window, respectively. The window is moved through the pressure-density data pairs (e.g., from low to high pressures) and at each location of the window (e.g., for each center $p_0$), the pressure-density data pairs falling within the window are fit to the example model of EQN (5).

The width of the window $p_w$ may be selected using any number and/or type(s) of criteria. To facilitate use of the example second-order model of EQN (5), the width $p_w$ is selected to include at least three pressure-density data pairs. When other order models (higher or lower) are used, the minimum number of data pairs that needs to be present in each window may need to be accordingly adjusted. For example, the first-order model of EQN (4) only requires two pressure-density data pairs in each window. In general, the use of additional data pairs increases the amount of filtering realized by the model. However, the use of an excessively wide window may result in a poor fit of the model to the pressure-density data pair(s) at the center pressure $p_0$ of the window. An example pressurization scheme changes (e.g., increases or decreases) the pressure p of fluid captured in the chamber 310 at a rate of 1000 pounds per square inch (psi) per minute. Using a window width $p_w$ of 500 psi and measuring the fluid density $\rho$ every second results in approximately 30 pressure-density data points in the window.

When the pressure-density data pairs falling within the window have been fit to the example model of EQN (5), the model parameter $a_1$ represents the filtered/smoothed density $\rho$ at pressure $p_0$, and the model parameters $a_2$ and $a_3$ represent the first and second derivatives of density $\rho$ with respect to pressure p at pressure $p_0$, respectively. The compressibility c of the fluid at pressure $p_0$ can be computed using the model parameters $a_1$ and $a_2$ using the following expression:

$$c = \frac{1}{\rho}\frac{\partial \rho}{\partial p}\bigg|_{p=p_0} = \frac{a_2}{a_1}. \quad \text{EQN (6)}$$

To fit the pressure-density data pairs to a model (e.g., the example model of EQN (5)), the example compressibility processor 320 of FIG. 3 includes a model fitter 335. The example model fitter 335 of FIG. 3 fits the pressure-density data pairs to example model of EQN (5) using any number and/or type(s) of criteria. For example, a least-squares criterion that minimizes ("min") the example summation term of EQN (7) may be used, where the values of $\rho_{meas}(p)$ are the measured pressure-density data pairs, and the values of $\rho_{mode}(p)$ are computed using EQN (5).

$$\min_{a_1, a_2, a_3} \sum_{p=p_0-p_w/2}^{p=p_0+p_w/2} (\rho_{meas}(p) - \rho_{model}(p))^2 \quad \text{EQN (7)}$$

Another example criterion comprises the least-absolute error criterion (i.e., the L1-norm), which minimizes the following example summation term:

$$\min_{a_1,a_2,a_3} \sum_{p=p_0-p_w/2}^{p=p_0+p_w/2} |\rho_{meas}(p) - \rho_{model}(p)|. \quad \text{EQN (8)}$$

In some examples, the L1-norm of EQN (8) is preferable to the least-squares criterion of EQN (7) due to its effectiveness at reducing the effect of noise spikes or other transients. Fitting of the pressure-density data pairs using the L1-norm of EQN (8) may be performed, for example, using the iterative re-weighted least-squares algorithm described in Generalized Linear Model, $2^{nd}$ Edition, authored by P. McCullagh and J. A. Nelder, and published by Chapman and Hall in 1989, which is hereby incorporated by reference in its entirety.

To output, store, display and/or otherwise present a fluid compressibility value determined by the compressibility processor 320, the example fluid analysis assembly 300 of FIG. 3 includes any number and/or type(s) of output devices, one of which is designated at reference numeral 340. In an example, the compressibility processor 320 computes a plurality of compressibility values for respective ones of a plurality of pressures, and a graph of the computed compressibility values versus the pressures are presented at a computer display 340. In another example, one or more compressibility values for corresponding pressures are printed at a printer 340. In yet another example, compressibility values and corresponding pressures are stored in a memory, a memory device and/or any other type of storage 340.

While an example manner of implementing a fluid analysis assembly 300 has been illustrated in FIG. 3, one or more of the elements, sensors, gauges, units, processes and/or devices illustrated in FIG. 3 may be combined, divided, re-arranged, omitted, eliminated, implemented in a recursive way, and/or implemented in any other way. Further, the example valve 305, the example chamber 310, the example pressure control unit 315, the example compressibility processor 320, the example pressure gauge 325, the example density sensor 330, the example model fitter 335, the example output device 340 and/or, more generally, the example fluid analysis assembly 300 of FIG. 3 may be implemented by hardware, software, firmware and/or any combination of hardware, software and/or firmware. Thus, for example, any or all of the example valve 305, the example chamber 310, the example pressure control unit 315, the example compressibility processor 320, the example pressure gauge 325, the example density sensor 330, the example model fitter 335, the example output device 340 and/or, more generally, the example fluid analysis assembly 300 may be implemented by one or more circuit(s), programmable processor(s), application specific integrated circuit(s) (ASIC(s)), programmable logic device(s) (PLD(s)) and/or field programmable logic device(s) (FPLD(s)), etc. Further still, a fluid analysis assembly may include elements, sensors, gauges, units, processes and/or devices instead of, or in addition to, those illustrated in FIG. 3 and/or may include more than one of any or all of the illustrated elements, sensors, gauges, units, processes and/or devices.

Figure 4:
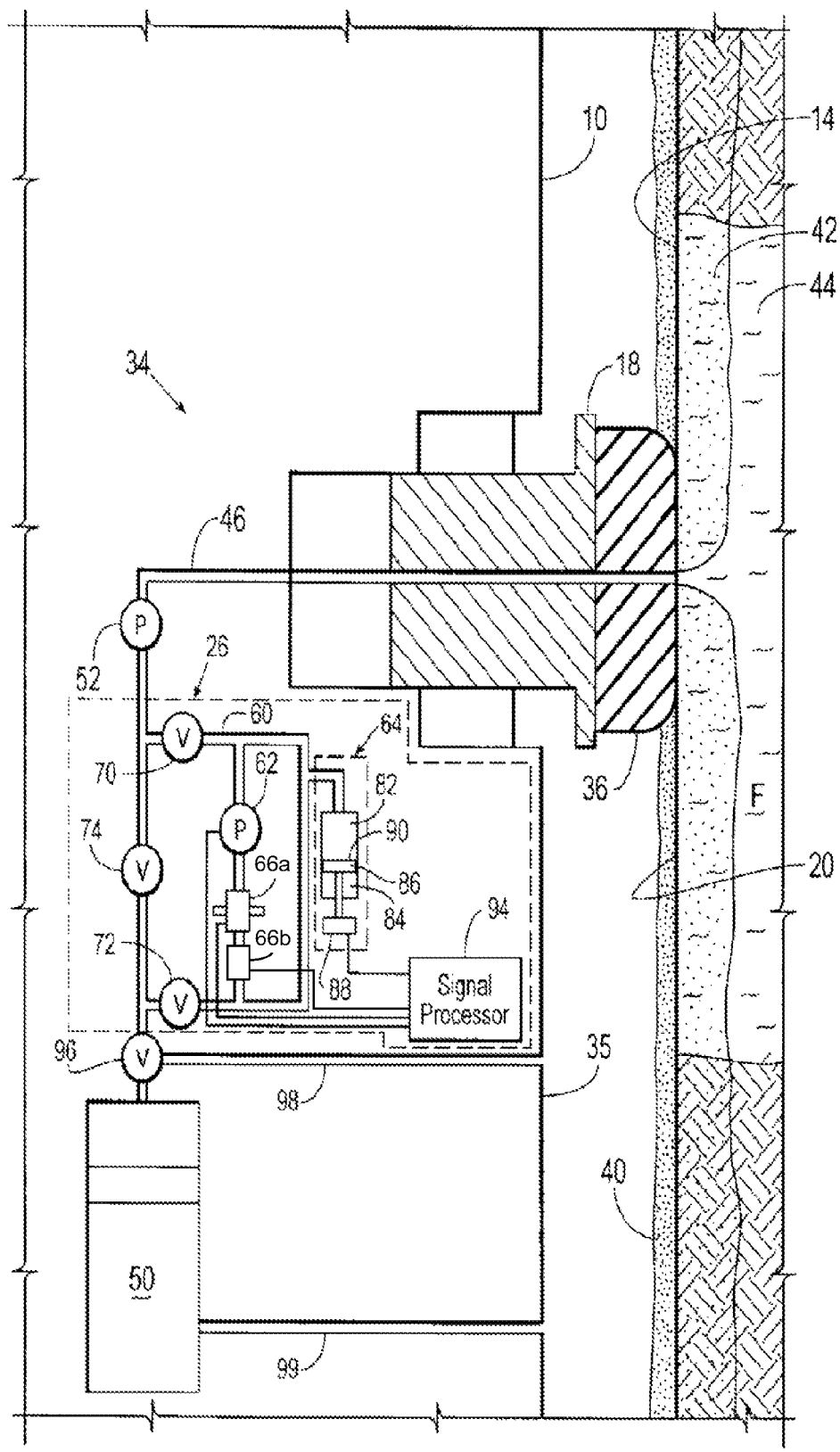
FIG. 4 illustrates an example manner of implementing any or all of the example fluid analysis assemblies of FIGS. 1-3.

FIG. 4 illustrates an example manner of implementing either or both of the example fluid analysis assemblies 26 and/or, more generally, a fluid flow system 34 for either or both of the example downhole tools 10 and 30 of FIGS. 1 and 2. For ease of discussion, the example fluid flow system 34 of FIG. 4 is described with reference to the example downhole tool 10. However, the example fluid flow system 34 may, additionally or alternatively, be used to implement a fluid flow system 34 for the example downhole tool 30.

The example probe 18 of FIG. 4 extends from a housing 35 of the downhole tool 10 for engagement with the wellbore wall 20. The probe 18 is provided with a packer 36 for sealing with the wellbore wall 20. The packer 36 contacts the wellbore wall 20 and forms a seal with a mud cake 40 lining the wellbore 14. The mud cake 40 gets deposited on the wellbore wall 20 due to seepage of mud and mud filtrate into the formation F. This seepage creates an invaded zone 42 about the wellbore 14. The invaded zone 42 contains mud filtrate and other wellbore fluids that contaminate the surrounding formations, including the formation F and a portion of the virgin fluid 44 contained therein.

The example fluid flow system 34 of FIG. 4 includes the evaluation flowline 46 extending from an inlet in the probe 18. While a probe 18 is depicted for drawing fluid into the downhole tool, other fluid communication devices may be used. Examples of fluid communication devices, such as probes and dual packers, used for drawing fluid into a flowline are depicted in U.S. Pat. Nos. 4,860,581 and 4,936,139.

The example evaluation flowline 46 of FIG. 4 extends into the downhole tool 10 and is used to pass fluid(s), such as virgin fluid 44 into the downhole tool 10 for pre-test, analysis and/or sampling. The example evaluation flowline 46 extends to a sample chamber 50 for collecting samples of the virgin fluid(s) 44. The example fluid flow system 34 of FIG. 4 may also include a pump 52 to draw fluid through the flowline 46.

While FIG. 4 shows an example configuration of a downhole tool 10 used to draw fluid from the formation F it will be appreciated by one of skill in the art that any number and/or type(s) of configurations of flowlines, pumps, sample chambers, valves and other devices may be used and is not intended to limit the scope of the invention.

As discussed above, the example downhole tool 10 of FIG. 4 includes the example fluid analysis assembly 26 to analyze formation fluid(s). In particular, the example fluid analysis assembly 26 of FIG. 4 is to effect downhole measurements, such as phase measurements, viscosity measurements, density measurements, pressure measurements and/or fluid compressibility determinations for the formation fluid. The example fluid analysis assembly 26 of FIG. 4 includes a fluid evaluation chamber 60, a fluid movement device 62, a pressure control assembly 64, and one or more sensors (two of which are designated at reference numerals 66a and 66b).

The example chamber 60 of FIG. 4 can have any configuration capable of receiving or capturing the formation fluid and permitting pressurization of the fluid as discussed herein so that pressure and density measurements can be effected. The example chamber 60 of FIG. 4 is implemented as a bypass flowline communicating with the evaluation flowline 46 such that formation fluid(s) can be positioned or diverted into the bypass flowline 60. In general, the example fluid evaluation chamber 60 includes all flowlines fluidly coupled to the chamber 60 and positioned to the right of valves 70 and 72, any fluids contained in any portion of the sensors 66a and/or 66b, and any fluid contained in the pressure control assembly 64. As used herein, the term "fluid contained in the chamber 60" refers to collectively to fluid contained in any of these devices.

The example fluid analysis assembly 26 of FIG. 4 includes a first valve 70, a second valve 72, and a third valve 74 for selectively diverting the formation fluid into and out of the chamber 60, as well as isolating the chamber 60 from the evaluation flowline 46.

To divert the formation fluid F into the chamber 60, the first valve 70, and the second valve 72 are opened, while the third valve 74 is closed. This diverts the formation fluid F into the chamber 60 while the pump 62 is moving the formation fluid F. Then, the first valve 70 and the second valve 72 are closed to isolate or trap the formation fluid F within the chamber 60. If desired, the third valve 74 can be opened to permit normal or a different operation of the downhole tool 10. For example, the valve 74 may be opened, and the valves 70 and 72 closed while the fluid in the chamber 60 is being evaluated. Additional valves and flowlines or chambers may be added as desired to facilitate the flow of fluid(s).

The example fluid movement device 62 of FIG. 4 is to move and/or mix the fluid within the chamber 60 to enhance the homogeneity and circulation of the fluid. Fluid is preferably moved through chamber 60 to enhance the accuracy of the measurements obtained by the sensor(s) 66a and/or 66b. In general, the fluid movement device 62 has a force medium applying force to the formation fluid to cause the formation fluid to be recirculated within the chamber 60.

The example fluid movement device 62 of FIG. 4 can be any type of device capable of applying force to the formation fluid to cause the formation fluid to be recirculated and optionally mixed within the chamber 60. For example, the fluid movement device 62 can be a positive displacement pump, such as a gear pump, a rotary lobe pump, a screw pump, a vane pump, a peristaltic pump, or a piston and progressive cavity pump.

Preferably, the example pressurization assembly 64 of FIG. 4 is to change the pressure of the formation fluid within the chamber 60 in preferably a continuous manner. The example pressurization assembly 64 can be any type of assembly or device capable of communicating with the chamber 60 and continuously changing (and/or step-wise changing) the volume or pressure of the formation fluid captured within the chamber 60. The example pressurization assembly 64 of FIG. 4 includes a decompression chamber 82, a housing 84, a piston 86, and a piston motion control device 88. The piston 86 is provided with an outer face 90, which cooperates with the housing 84 to define the decompression chamber 82. The piston motion control device 88 controls the location of the piston 86 within the housing 84 to effectively change the volume of the decompression chamber 82.

As the volume of the decompression chamber 82 changes, the volume and pressure within the chamber 60 also change. Thus, as the decompression chamber 82 becomes larger, the pressure within the chamber 60 is reduced. Likewise, when the decompression chamber 82 becomes smaller, the pressure within the chamber 60 is increased. The piston motion control device 88 can be any type of electronic and/or mechanical device capable of effecting changes in the position of the piston 86. For example, the piston motion control device 88 can be a pump exerting on a fluid on the piston 86, or a motor operably connected to the piston 86 via a mechanical linkage, such as a post, flange, or threaded screw.

The example sensor 66a of FIG. 4 is any type of pressure sensing device capable to measure and/or record the pressure p of the fluid captured in the chamber 60. An example pressure sensing sensor 66a is a micro-sapphire sensor.

The example sensor 66b of FIG. 4 is any type of density sensor capable to measure and/or determine the density of the fluid captured in the chamber 60. An example density sensor 66b comprises a vibrating rod, and electronics for actuation and detection. As is well known in the art, the resonance characteristic(s) of a vibrating rod oscillating in a fluid may used to determine, measure, compute and/or otherwise detect the density of the fluid in which the vibrating rod oscillates.

The example fluid analysis assembly 26 of FIG. 4 is also provided with a signal processor 94 communicating with the fluid movement device 62, the sensor(s) 66a and 66b, and the piston motion control device 88. The signal processor 94 preferably controls the piston motion control device 88, and the fluid movement device 62 for effecting movement of the formation fluid within the chamber 60. The processor 94 may also change the pressure of the formation fluid in a predetermined manner (e.g., decreasing the pressure at a rate of 1000 psi/minute). The signal processor 94 can control the piston motion control device 88 in a continuous manner, a stepped manner, or combinations thereof.

The example signal processor 94 of FIG. 4 also collects and/or manipulates data produced by the sensor(s) 66a and 66b. For example, the signal processor 94 can control the piston motion control device 88 to transition the fluid captured in the fluid evaluation chamber at or through a plurality of pressures. While the fluid is being pressurized at the plurality of pressures, the signal processor 94 collects corresponding pairs of pressure measurements and fluid density measurements. Using methods described above in connection with the example compressibility processor 320 of FIG. 3, the example signal processor 94 of FIG. 4 can compute fluid compressibility values using the collected pressure-density data pairs. Additionally or alternatively, the signal processor 94 records the pressure-density data pairs and transmits and/or retrieves the data pairs to the surface where a compressibility module 320 computes fluid compressibility values. Further still, a fluid sample can be captured in the bottle 50 and retrieved to the example fluid analysis assembly 300 of FIG. 3 to measure pressure-density data pairs and determine fluid compressibility values. Such analysis may be performed at the wellsite, in a transportable lab and/or at a fixed-location lab.

The example signal processor 94 of FIG. 4 can communicate with the fluid movement device 62, the sensor(s) 66a and 66b, and/or the piston motion control device 88 via any suitable communication link, such as a cable or wire communication link, an airway communication link, infrared communication link, microwave communication link, or the like. Although the example signal processor 94 is illustrated as being within the housing 35 of the downhole tool 10, it should be understood by that the signal processor 94 can be provided remotely with respect to the downhole tool 10. For example, the signal processor 94 can be provided at a monitoring station located at the wellsite, or located remotely from the wellsite. The signal processor 94 includes one or more electronic or optical device(s) capable of executing the logic to effect the control of the fluid movement device 62, and the piston motion control device 88, as well as to collect, store or manipulate information from the sensor(s) 66a and 66b described herein. The signal processor 94 can also communicate with and control the first valve 70, the second valve 72, and the third valve 74 to selectively divert fluid into and out of the chamber 60 as discussed above. For purposes of clarity, lines showing the communication between the signal processor 94 and the first valve 70, the second valve 72 and the third valve 74 have been omitted from FIG. 4.

The example downhole tool 10 of FIG. 4 also includes a fourth valve 96 for selectively diverting the formation fluid into the sample chamber 50, or to the wellbore 14 via a flowline 98. The downhole tool 10 may also be provided with an exit port 99 extending from a backside of sample chamber 50.

Figure 5:
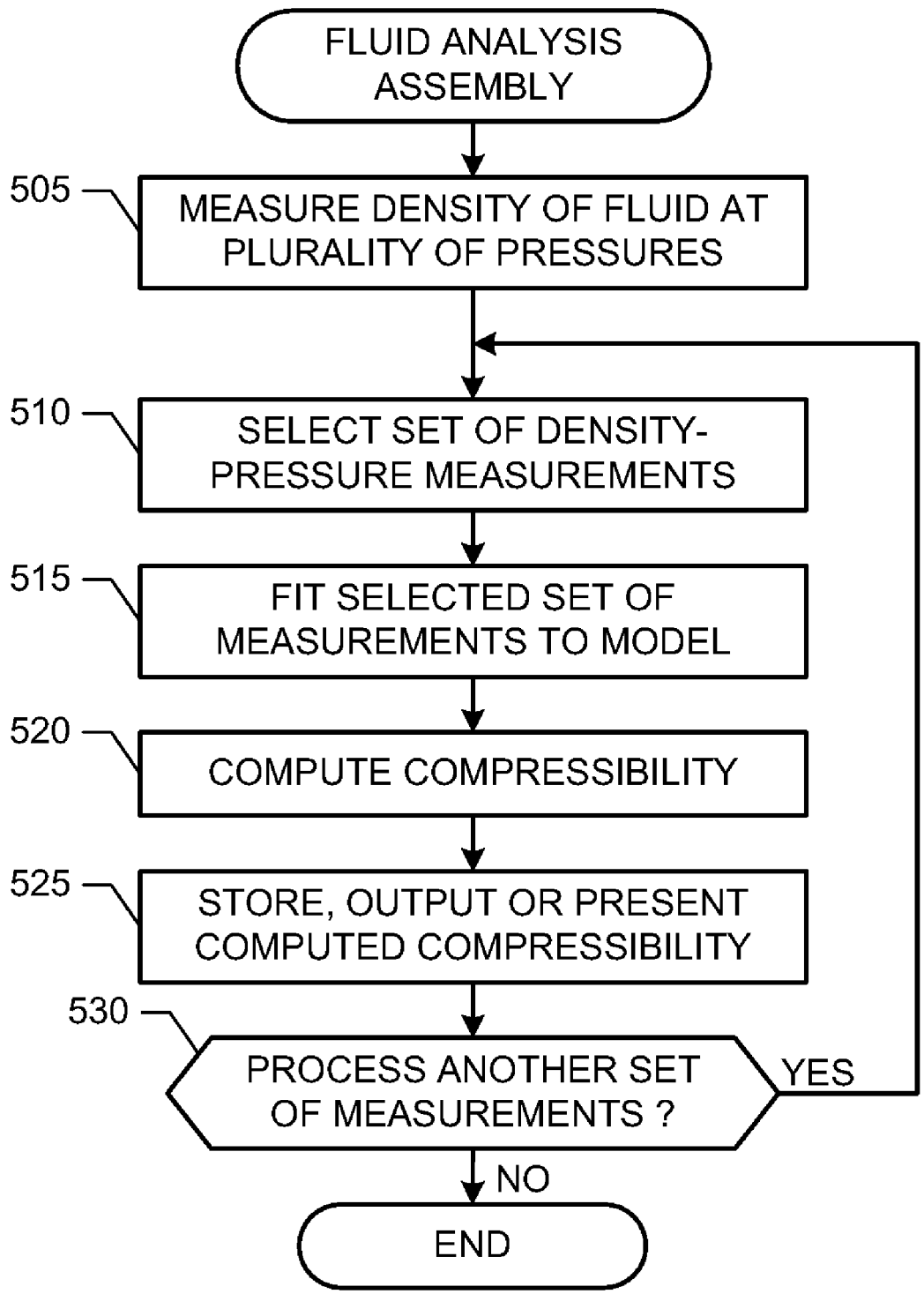
FIG. 5 illustrates an example process that may be carried out to determine the compressibility of a fluid, and/or to implement any or all of the example fluid analyzers of FIGS. 1-4.

FIG. 5 illustrates an example process that may be carried out to implement any or all of the example fluid analysis assemblies 300 of FIG. 3. While the example process of FIG. 5 is described with reference to the example fluid analysis assembly 300 of FIG. 3, the example process of FIG. 5 may be used to, additionally or alternatively, implement the example fluid analysis assembly 26 of FIGS. 1, 2 and 4. The example process of FIG. 5 may be carried out by a processor, a controller and/or any other suitable processing device. For example, the process of FIG. 5 may be embodied in coded instructions stored on a tangible medium such as a flash memory, a read-only memory (ROM) and/or random-access memory (RAM) associated with a processor (e.g., the example processor P105 discussed below in connection with FIG. 8). Alternatively, some or all of the example process of FIG. 5 may be implemented using any combination(s) of circuit(s), ASIC(s), PLD(s), FPLD(s), discrete logic, hardware, firmware, etc. Also, some or all of the example process of FIG. 5 may be implemented manually or as any combination of any of the foregoing techniques such as, for example, any combination of firmware, software, discrete logic and/or hardware. Further, although the example operations of FIG. 5 are described with reference to the flowchart of FIG. 5, many other methods of implementing the operations of FIG. 5 may be employed. For example, the order of execution of the blocks may be changed, and/or one or more of the blocks described may be changed, eliminated, sub-divided, or combined. Additionally, any or all of the example process of FIG. 5 may be carried out sequentially and/or carried out in parallel by, for example, separate processing threads, processors, devices, discrete logic, circuits, etc.

The example process of FIG. 5 begins with the example compressibility processor 320 of FIG. 3 controlling the example pressure control unit 315 to pressurize a fluid captured in the chamber 310 at a plurality of pressures, and collecting corresponding pairs of pressures p and fluid densities ρ from the example pressure gauge 325 and the example density sensor 330, respectively (block 505). The compressibility processor 320 selects a set of the pressure-density data pairs using, for example, a sliding window (block 510). The example model fitter 335 fits the selected pressure-density data pairs to a model (e.g., either the example models of EQN (3) and/or EQN (5)) (block 515). Using one or more parameters of the model, the example compressibility processor 320 determines a fluid compressibility c for the center pressure $p_0$ of the window using, for example, EQN (6) (block 520). The compressibility processor 320 presents, outputs, displays, prints, and/or stores the computed compressibility c for later retrieval (block 525). If there are additional pressure-density data pairs to process (e.g., another window location to process), control returns to block 510 (block 530). If there are no additional pressure-density data pairs to process (block 530), control exits from the example process of FIG. 5.

Figure 6:
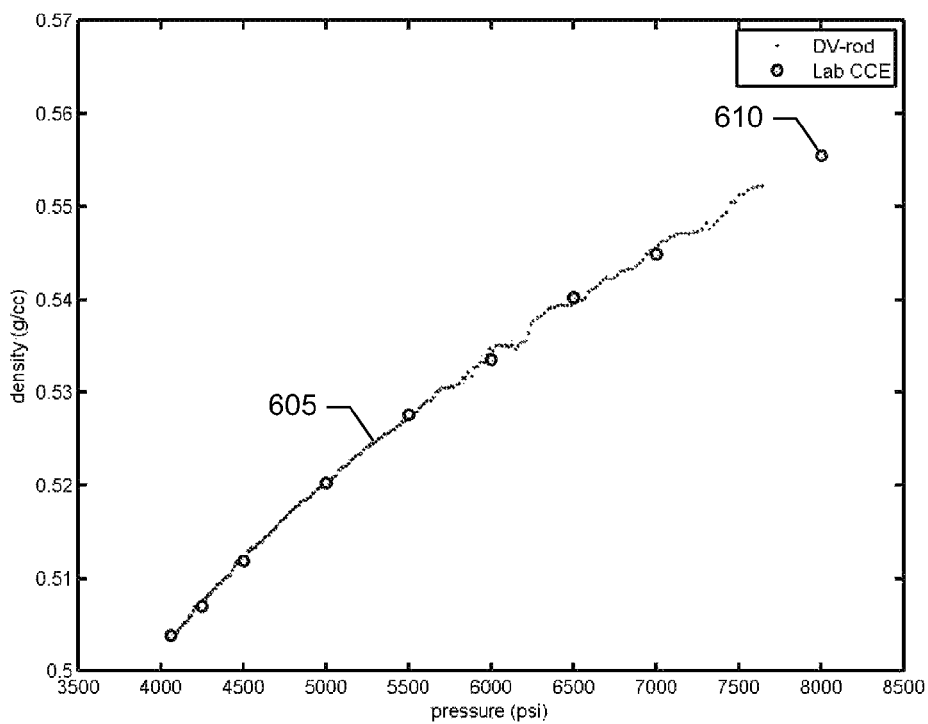
FIGS. 6 and 7 are graphs illustrating example fluid compressibility results determined used the example methods or apparatus disclosed herein.

FIG. 6 is a graph illustrating example pressure-density data 605 collected using the example fluid analysis assembly 26 of FIG. 3. The example graph of FIG. 6 shows fluid densities ρ for respective ones of pressures p. In the example of FIG. 6, the pressure-density data 605 is compared with pressure-density data 610 measured using a constant composition expansion (CCE) procedure. The CCE procedure is a well-known laboratory technique used to analyze the fluid properties of a fluid captured in a sample bottle or container. The example CCE procedure of FIG. 6 was performed on the same fluid that was captured by the example fluid analysis assembly 26. As shown, the measured pressure-density data 605 is nearly identical to the CCE based pressure-density data 610.

Figure 7:
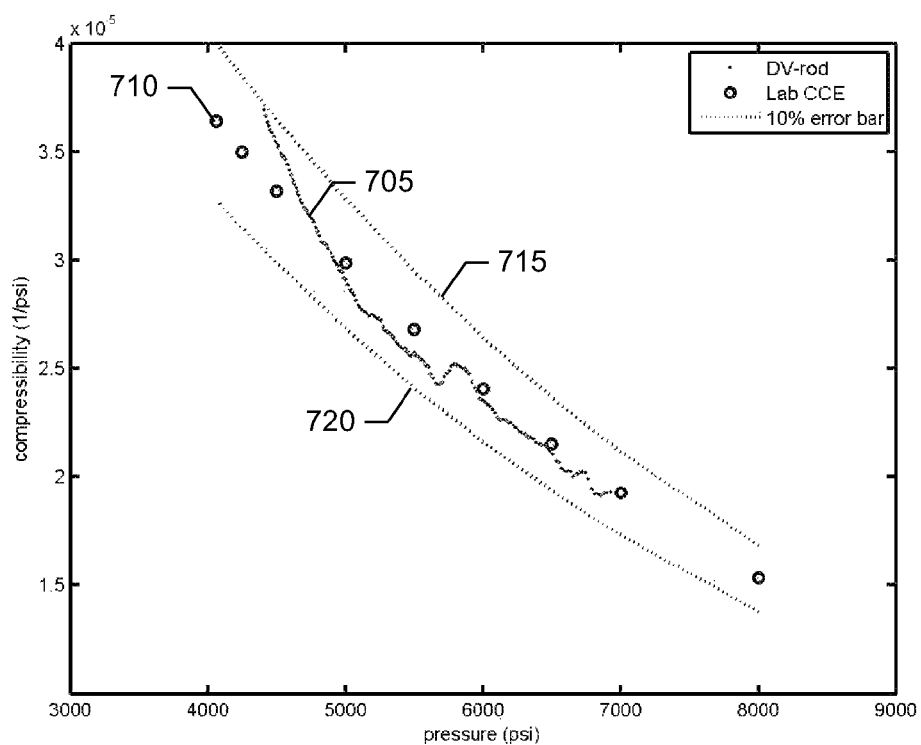

FIG. 7 is a graph illustrating example compressibility values 705 computed by the example compressibility processor 320 of FIG. 3 using the example pressure-density data 605 of FIG. 6. Also shown in FIG. 7 are compressibility values 710 measured using a CCE procedure, as well as curves 715 and 720 representing 10% deviations from the curve 710. The example CCE procedure of FIG. 7 was performed on the same captured fluid that was analyzed by the example compressibility processor 320. As demonstrated in FIG. 7, compressibility values 705 computed using the example fluid analysis assembly 300 of FIG. 3 correlate very well with the CCE measured values 710.

Figure 8:
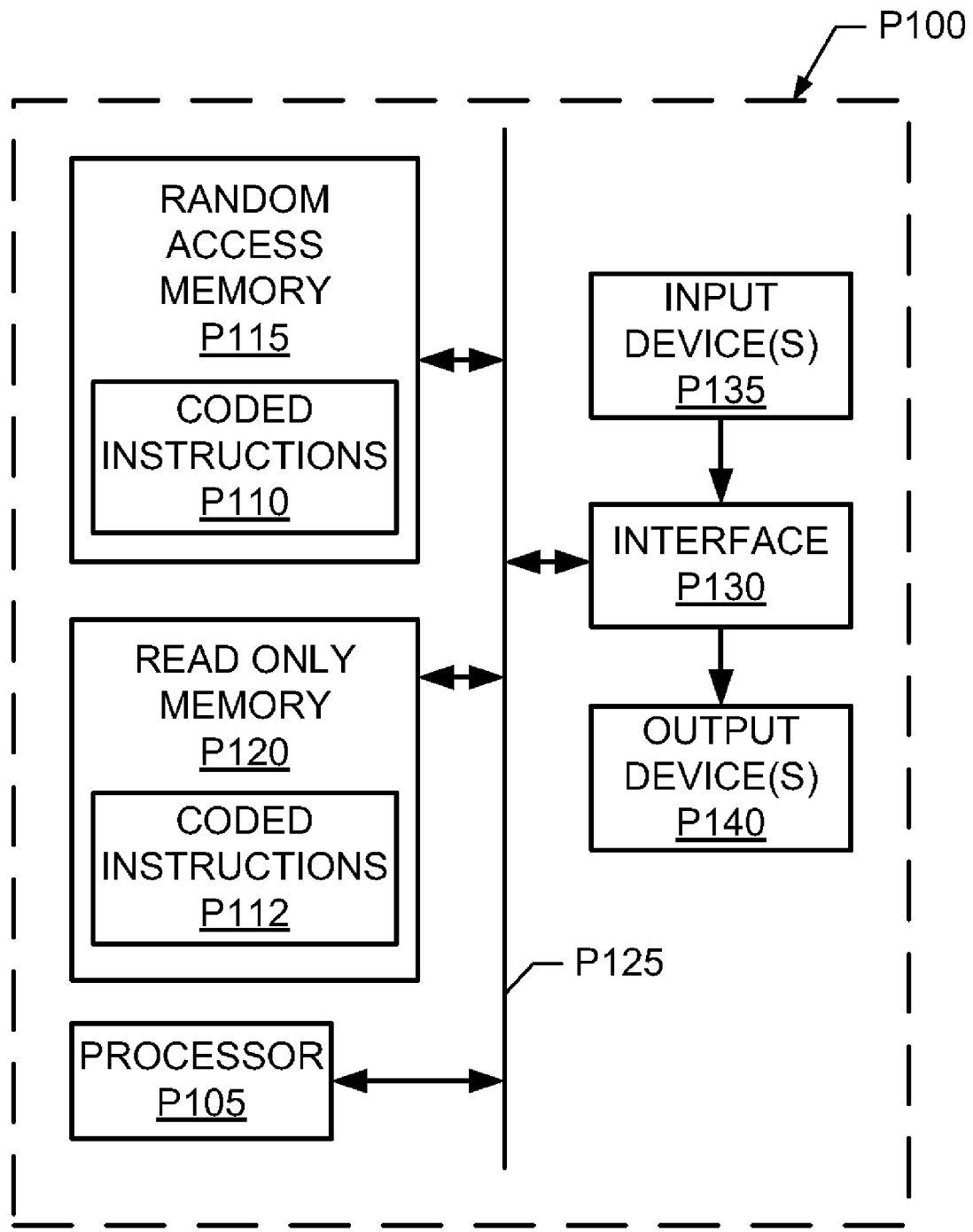
FIG. 8 is a schematic illustration of an example processor platform that may be used and/or programmed to implement the example fluid analysis assemblies of FIGS. 1-4, and/or to carry out the example process of FIG. 5.

FIG. 8 is a schematic diagram of an example processor platform P100 that may be used and/or programmed to implement the example signal processor 94 and/or all or a portion of any or all of the example fluid analysis assemblies 26, 300 disclosed herein. For example, the processor platform P100 can be implemented by one or more general-purpose processors, processor cores, microcontrollers, etc.

The processor platform P100 of the example of FIG. 8 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example process of FIG. 5 to implement the example methods and apparatus described herein.

The processor P105 is in communication with the main memory (including a ROM P120 and/or the RAM P115) via a bus P125. The RAM P115 may be implemented by dynamic random-access memory (DRAM), synchronous dynamic random-access memory (SDRAM), and/or any other type of RAM device, and ROM may be implemented by flash memory and/or any other desired type of memory device. Access to the memory P115 and the memory P120 may be controlled by a memory controller (not shown). The memory P115, P120 may be used to, for example, pressure values, density values and/or compressibility values.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The example output device P140 may be used to, for example, control the example pressure control units 315, 88, and/or output, display and/or otherwise present pressure values, density values and/or compressibility values. The example input device P135 may be used to, for example, collect data from the example pressure gauges 325, 66a and/or the example density sensors 330, 66b Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. A method comprising:
capturing a fluid in a chamber;
pressurizing the captured fluid to first and second pressures;
measuring first and second values representative of first and second densities of the fluid while pressurized at respective ones of the first and second pressures; and
computing a third value representative of a compressibility of the fluid using the first and second values.

2. A method as defined in claim 1, further comprising vibrating a rod to measure the first value.

3. A method as defined in claim 1, wherein computing the third value comprises computing a derivative using the first and second values and the first and second pressures.

4. A method as defined in claim 1, further comprising:
pressurizing the captured fluid to a third pressure;
measuring a fourth value representative of a third density of the fluid while pressurized at the third pressure; wherein the third value is computed using the first, second and fourth values; and
storing the third value.

5. A method as defined in claim 4, wherein computing the third value comprises:
fitting the first, second and fourth values to a second-order polynomial model; and
computing a ratio of a first and second parameter of the model.

6. A method as defined in claim 5, further comprising using a least-absolute error criterion to fit the model to the first, second and fourth values.

7. A method as defined in claim 1, wherein the chamber comprises a flowline of a downhole tool.

8. A method as defined in claim 7, wherein the fluid is pressurized to the first pressure and the first value is measured while the downhole tool is located in a wellbore.

9. A method as defined in claim 7, wherein the third value is computed while the downhole tool is located in a wellbore.

10. A fluid analysis apparatus comprising:
a chamber;
a pressure control unit to pressurize a fluid contained in the chamber at first and second pressures;
a density sensor to measure first and second values representative of first and second densities of the fluid while pressurized at respective ones of the first and second pressures; and
a compressibility module to compute a third value representative of a compressibility of the fluid based on the first and second values.

11. A fluid analysis apparatus as defined in claim 10, further comprising:
a pressure sensor to measure fourth and fifth values representative of the first and second pressures; and
an output device to at least one of display, present, or store the third value.

12. A fluid analysis apparatus as defined in claim 10, wherein the density sensor comprises a vibrating rod.

13. A fluid analysis apparatus as defined in claim 10, wherein the pressure control unit is to pressurize the fluid to a plurality of additional pressures, the density sensor is to measure a plurality of values representative of additional densities of the fluid while pressurized at respective ones of the plurality of additional pressures, and the compressibility module is to compute the third value using the first value, the second value and the plurality of values.

14. A fluid analysis apparatus as defined in claim 10, wherein the density sensor is to operate while fluid sampling apparatus is positioned in a wellbore.

15. A fluid analysis apparatus as defined in claim 10, further comprising a sampling container to store a sample of the fluid.

16. A fluid analysis apparatus as defined in claim 10, wherein the chamber comprises a flowline of a downhole tool.

17. A fluid analysis apparatus as defined in claim 10, wherein the compressibility module is to compute the third value as a derivative of the first and second values and the first and second pressures.

18. A fluid analysis apparatus as defined in claim 10, wherein the pressure control unit is to pressurize the fluid to a third pressure, the density sensor is to measure a fourth value representative of a third density of the fluid while pressurized at the third pressure, and the compressibility module is to compute the third value using the first, second and fourth values.

19. A fluid analysis apparatus as defined in claim 18, wherein the compressibility module comprises a model fitter to determine first and second model parameters using the first, second and fourth values, and wherein the third value comprises a ratio of the first and second model parameters.

20. A fluid analysis apparatus as defined in claim 19, wherein the model fitter performs at least one of a least-squares fit or a least-absolute error fit to determine the first and second model parameters.

* * * * *